United States Patent [19]

Broomes

[11] 4,366,815

[45] Jan. 4, 1983

[54] ANTI-SNORING APPARATUS

[76] Inventor: Edward L. C. Broomes, 2301 Lituanica, East Chicago, Ind. 46312

[21] Appl. No.: 270,380

[22] Filed: Jun. 4, 1981

[51] Int. Cl.³ .......................................... A61F 13/12
[52] U.S. Cl. .................................................. 128/164
[58] Field of Search ............... 128/134, 135, 136, 164, 128/75, DIG. 23

[56] References Cited

U.S. PATENT DOCUMENTS

| | | | |
|---|---|---|---|
| 1,216,679 | 2/1917 | Foster | 128/164 |
| 1,910,328 | 5/1933 | Glennan | 128/DIG. 23 |
| 1,990,411 | 2/1935 | Lowry | 128/136 X |
| 2,711,730 | 6/1955 | Rogers | 128/164 |
| 3,696,810 | 10/1972 | Gaylord, Jr. | 128/75 |

Primary Examiner—John D. Yasko
Attorney, Agent, or Firm—Irwin C. Alter

[57] ABSTRACT

An apparatus for preventing a sleeping person from snoring while permitting normal, comfortable sleep, comprising a flexible cylindrically shaped body means designed to be worn in proximity to the user's neck and beneath the user's chin. Said cylindrically shaped body means is designed with a cross-sectional diameter sufficient at that portion which is worn beneath the user's chin to restrict forward cervical vertebral flexion, while permitting substantial flexibility of the neck in other directions to maximize comfort and permit normal sleep. The cylindrically shaped body means has a first end and a second end restrained within proximity to a plane tangential to the rear of the user's neck by a connecting device, yet displaced from immediate proximity to the back of the neck and head whereby said first and second ends of said body means do not encroach between said user's neck and the associated bedding, thereby permitting normal repose. Said cylindrically shaped body means is maintained in the appropriate orientation and proximity to the user's neck and chin by attachment straps passing around the user's neck or around the user's head and adjustably attached by suitable fastening means.

9 Claims, 7 Drawing Figures

ANTI-SNORING APPARATUS

BACKGROUND OF THE INVENTION

The present invention relates, in general, to neck collars and, particularly, to an anti-snoring device for maintaining almost erect the head of the sleeper so that the chin does not slump on the chest.

Snoring is a rough, hoarse noise produced by the vibration of air waves passing through a partially obstructed trachea. The trachea is the main trunk of a system of tubes through which air passes to and from the lungs. When the head is held erect, air passes through the trachea unimpededly. However, if the head and neck are flexed, the trachea also becomes flexed. There is then created, at the point of flexion, a point of partial obstruction. Air passing through this point of partial obstruction causes vibration which produce the unpleasant sound referred to as snoring. The trachea can become flexed when a person is sleeping. Such a condition can occur when the head of the sleeper droops and the chin rests on the chest. By elevating the chin away from the chest, the trachea is straightened and the problem is solved. The effectiveness of the principle of elevating the chin is demonstrated by the fact that in all life threatening situations involving asphyxia, this procedure is mandated as the first step before artificial respiration is to be administered. A further support of the theory is in drawing attention to the fact that no one snores when awake even if lying in bed; because when awake, the head subconsciously is kept elevated away from the chest by the pulley action of the muscles at the back of the neck. This control is relaxed during unconsciousness.

When the present theory embodied in this invention was first expressed, it was presented as a suggestion, without any critical study, that the ordinary flat cervical collar used for sprained necks might also serve as a device to keep the chin elevated. Subsequent observation soon demonstrated that the principle which determined the effectiveness of the flat collar in relieving the pains of a sprained neck, is diametrically opposite to that which would make an anti-snoring device useful. In the former, the intended purpose is primarily to restrict the movement of the head from side to side; since in neck sprains, downward movement of the head does not cause much pain. To be truly effective, the sprain collar must be wide enough to envelope at least the lower portion of the chin to immobilize the head. When this, however, has been attained, it is then easy for the chin to slip downwards between the edges of the enveloping collar and still rest on the chest, thereby militiating against its use as an effective and dependable anti-snoring device. In addition, such collars substantially restrict movement of the head and neck in all directions, and therefore are uncomfortable to wear and interfere with normal sleep of the wearer. Specifically, whereas it is the forward flexion of the cervical vertibrae that creates the restriction of the trachea leading to snoring, such existing collars contrastingly restrict side and back flexion of the neck unnecessarily.

Accordingly, the present invention has, as an object, the provision of an anti-snoring apparatus which maintains the chin markedly above the sleeper's chest.

It is a further object of the invention to provide a flexible anti-snoring apparatus.

Still another object of the invention is to provide an anti-snoring apparatus which is held securely around and under the neck and under the chin.

Yet, another object of the invention is to provide an anti-snoring apparatus which is simple to construct and reliable in its use.

A further object of the present invention is to provide such advantageous functions while not unduly or unnecessarily restricting other normal movement of the head or neck to thereby maximize the comfort and acceptability of the apparatus and permit normal sleep.

These and other objects of the invention will become apparent upon consideration of the accompanying specification and drawings.

SUMMARY OF THE INVENTION

The present invention comprises an anti-snoring apparatus for preventing a sleeping person from making snoring sounds.

The apparatus comprises a cylindrically shaped body which encircles a sleeper's neck. Because the apparatus is to be worn while sleeping, the cylindrical body has a cross-sectional diameter so calculated as to allow free side-to-side movements of the head, yet, prevent its downward flexion on the chest. The cylindrical body has a first and second end. Extending from each such end is a connecting cord keeping each such end in close proximity at the rear of the sleeper's neck. The apparatus is attached around the user's neck by straps. These straps maintain the cylindrical body, intermediate the first end and second end, beneath the user's chin. In one embodiment of the invention, neck straps are provided, which adjust to the diameter of the user's neck. In a second embodiment, head straps are provided which adjust to diameter of the user's head.

The apparatus is a flexible collar having a resilient core covered with a soft, absorbent fabric. The resilient core can be made from foam rubber and the soft fabric can be satin.

The attachment straps each has a first end attached to the cylindrical body. The second end of each strap has a hook-and-loop fastening material attached thereto. When the straps are attached together, the anti-snoring apparatus is maintained securely and comfortably beneath the user's chin.

Snoring is caused by the passage of air through a partially obstructed trachea. This can occur during sleep when the head slumps or droops on the chest. Therefore, an effective way to eliminate snoring is by elevating the chin from the chest. This must be done in a comfortable manner so as not to interrupt the sleeping person. The present apparatus allows free movement of the head and neck in all directions with the exception of downwards. Therefore, a person can comfortably sleep without disturbing others by snoring. The anti-snoring device will prevent the sleeper from snoring and not the snorer from sleeping.

DETAILED DESCRIPTION OF THE DRAWINGS

Figure 1:
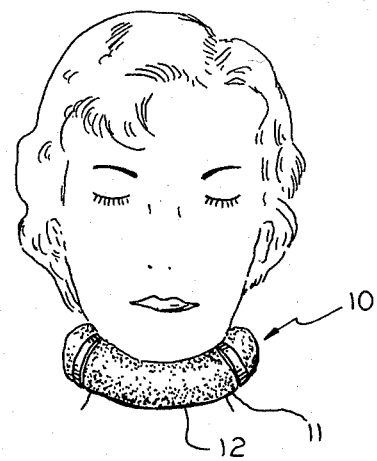
FIG. 1 is a front elevational view showing, particularly, the orientation of the anti-snoring apparatus surrounding a user's neck.

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiments illustrated.

A preferred embodiment of the invention is shown in FIG. 1, where anti-snoring apparatus 10 has a cylindrically shaped body 11 surrounding the user's neck. The cylindrically shaped body 11 is covered by a soft fabric 12 so as not to irritate user's skin.

Figure 2:
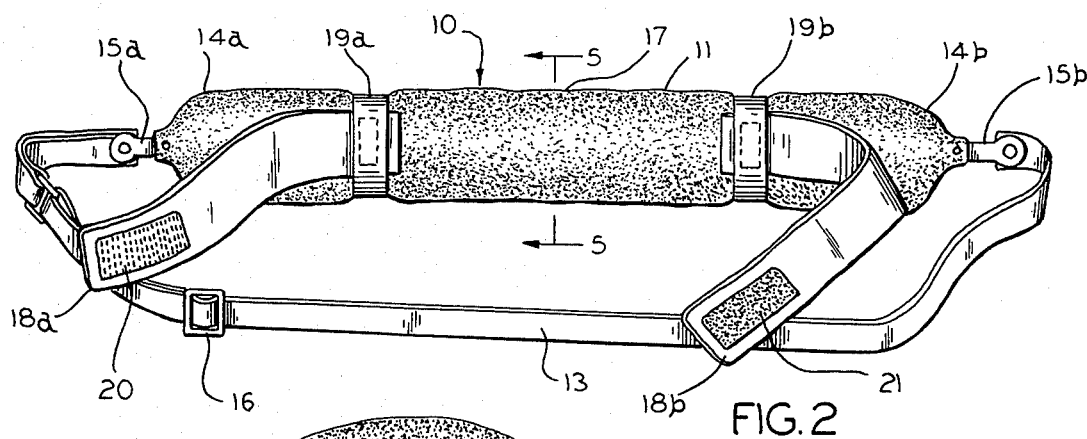
FIG. 2 is a rear elevational view of the anti-snoring apparatus in an unflexed position, showing, particularly, the neck attachment straps and adjustable end cord.

The rear elevational view of FIG. 2 shows cylindrically shaped body 11 in an unflexed position. Body ends 14a and 14b are held at the rear of user's neck by cord 13. Cord 13 attaches to body ends 14a and 14b by end connectors 15a and 15b. Because anti-snoring apparatus 10 must fit comfortably around user's neck, clasp 16 is provided to effectively adjust the length of cord 13.

The mid-point 17 of cylindrically shaped body 11 is maintained under user's chin by neck attachment straps 18a and 18b. Restraining bands 19a and 19b surround cylindrically shaped body 11 and secure neck attachment straps 18a and 18b thereto. Neck attachment straps 18a and 18b attach to each other at the rear of the user's neck by means of a hook-and-loop fastening method. A multiplicity of hooks 20 attach to neck attachment strap 18a and cooperate with a multiplicity of loops 21 attached to neck attachment strap 18b. The fastener can be adjusted to comfortably maintain midpoint 17 beneath user's chin.

Figure 3:
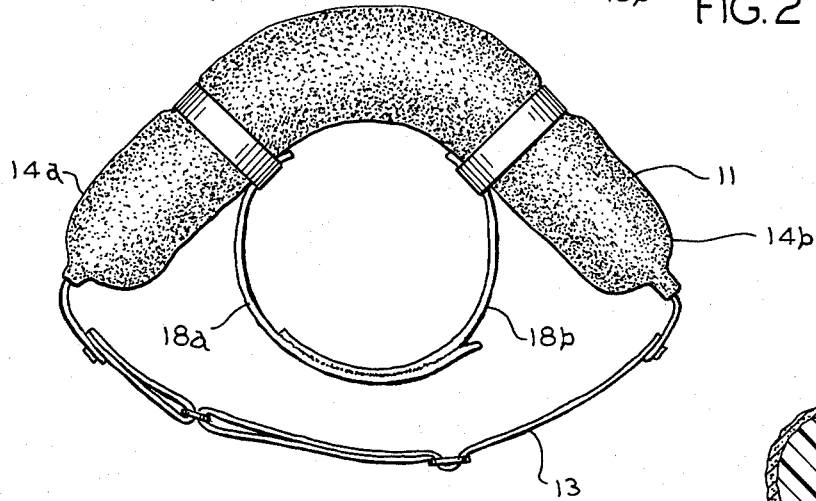
FIG. 3 is a top view of the neck attachment straps and the anti-snoring apparatus in an unflexed position.

In the top view of FIG. 3, cylindrically shaped body 11 is shown in a flexed position. This flexed position is maintained by attaching neck attachment straps 18a and 18b to each other, and effectively shortening cord 13. Body ends 14a and 14b do not join together directly at the rear of user's neck. Rather, they are connected by cord 13. This allows for more comfort in wearing of the anti-snoring device 10 while lying on the back and so does not prevent the user from sleeping.

Figure 4:
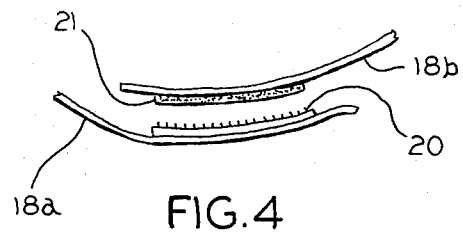
FIG. 4 is an enlarged view of the hook-and-loop fasteners on the attachment straps.

FIG. 4 is an enlarged view of the fasteners attached to neck attachment straps 18a and 18b. The diameter of the user's neck will determine the overlap of the loop portion 21 with the hook portion 20.

Figure 5:
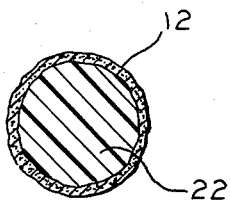
FIG. 5 is a cross-sectional view of the anti-snoring apparatus shown in FIG. 2.

The cross-sectional view of FIG. 5 shows soft fabric cover 12 surrounding foam rubber core 22 of cylindrically shaped body 11. The foam rubber core 22 will compress when user's head is moved, however, cylindrically shaped body 11 is non-collapsible and will prevent user's chin from contacting user's chest.

Figure 6:
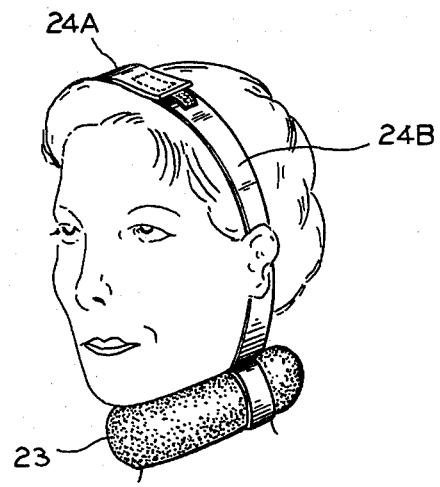
FIG. 6 is a front elevational view showing, particularly, the orientation of the anti-snoring apparatus having head attachment straps.

A second embodiment of the invention is shown in FIG. 6, where cylindrically shaped body 23 has head attachment straps 24a and 24b. The head attachment straps 24a and 24b are positioned behind the user's ears and attach to each other on top of the user's head.

Figure 7:
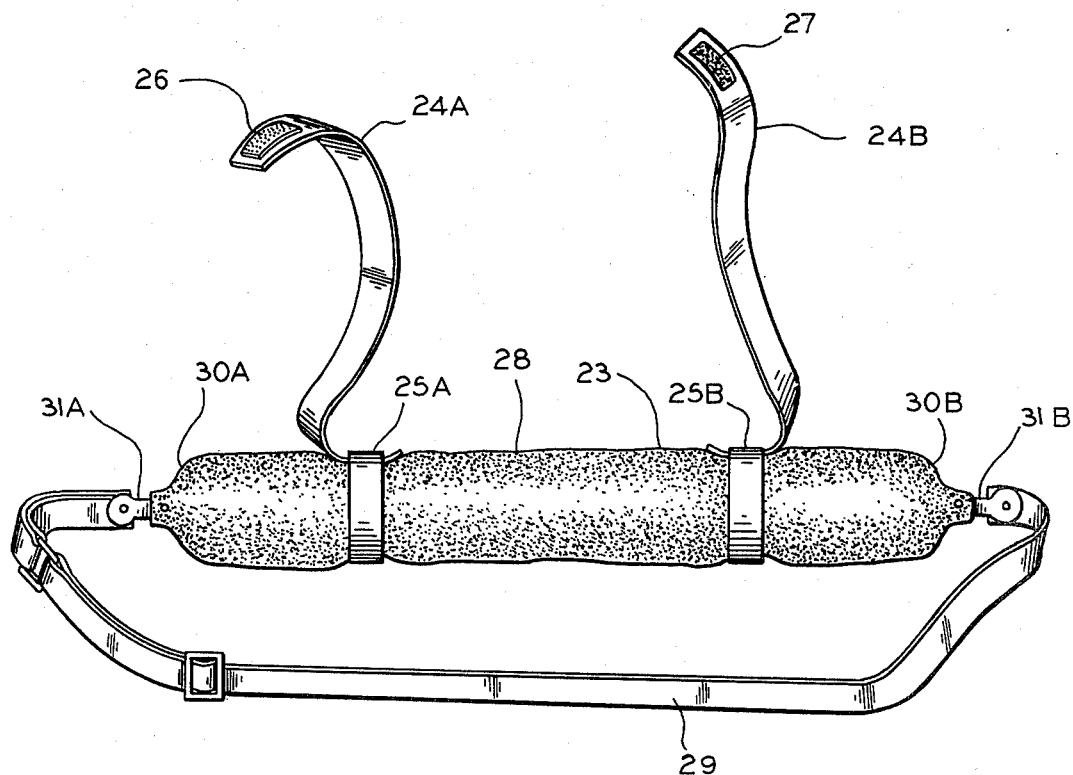
FIG. 7 is a rear elevational view of the anti-snoring apparatus in an unflexed position, showing, particularly, the head attachment straps and adjustable end cord.

The rear elevational view shown in FIG. 7 shows body 23 in an unflexed position. Cylindrically shaped body 23 has head straps 24a and 24b attaching to restraining bands 25a and 25b. Head straps 24a and 24b attach to each other across the top of the user's head by means of a hook-and-loop fastening means. A multiplicity of hooks 26 attached to head strap 24a, cooperate with a multiplicity of loops 27, attached to head strap 24b. Head straps 24a and 24b maintain midpoint 28 securely beneath the user's chin. Cord 29 attaches to body ends 30a and 30b by end connectors 31a and 31b and maintains body ends 30a and 30b at rear of user's neck.

Anti-snoring apparatus is constructed to be lightweight and comfortable to wear when sleeping. It allows free rotation of the user's head and does not immobilize the user's cervical vertebrae. The anti-snoring apparatus maintains a clear airway through user's trachea by preventing user's chin from coming in contact with user's chest. An unobstructed trachea will allow a sleeping person to inspire and expire air without making a snoring sound.

The foregoing description and drawings merely explain and illustrate the invention and the invention is not limited thereto except insofar as the appended claims are so limited as those skilled in the art having the disclosure before them will be able to make modifications and variations therein without departing from the scope of the invention.

What is claimed is:

1. An apparatus for maintaining the user's chin in an elevated position during sleep to prevent snoring while otherwise not restricting displacement of the user's head or neck, said apparatus comprising:
   cylindrically shaped body means;
   said cylindrically shaped body means having a cross-sectional diameter at its center portion sufficient to intercede between the user's chin and chest to restrict forward flexion of the cervical vertibrae of the user;
   said cylindrically shaped body means having a cross-sectional area at all portions other than said central portion sufficiently narrow to permit substantial side flexion of the cervical vertibrae of said user;
   said cylindrical shaped body means being substantially flexible throughout its length;
   end connection means extending from the first and from the second end of said cylindrically shaped body means;
   said end connection means attached to and spanning between said first and second ends of said cylindrically shaped body means;
   attachment means affixed to said cylindrically shaped body means for maintaining said center portion of said cylindrically shaped body means proximate to said user's neck and substantially centered and secured beneath said user's chin;
   said cylindrically shaped body means comprising a resiliant core; and
   said cylindrically shaped body means including soft, absorbent, flexible covering.

2. The invention according to claim 1 in which said flexible covering comprises satin material.

3. The invention according to claim 1 in which said resiliant core comprises foam rubber.

4. The invention according to claim 1 in which said end connection means comprises elastic strap means.

5. The invention according to claim 1 in which said end connection means includes length adjusting means, whereby said first and second ends of said cylindrically shaped body means may be selectively restrained at a chosen separation, said separation corresponding to the length of said end connection means and being adjustable between a first, minimum separation and a second, maximum separation such that said first and second ends of said cylindrically shaped body means may be restricted within the proximity of a plane tangential to the back of said user's neck, yet may selectively maintain sufficient separation to permit said first and second ends of said cylindrically shaped body means to extend away from the side and back portion of said user's neck.

6. The invention according to claim 1 in which said attachment means comprises:
  dual neck strap means for passing around the user's neck, each of said neck strap means having a respective first and second end;
  said first end of the first of said dual neck strap means being affixed to said cylindrically shaped body means at a point intermediate to said center portion of said cylindrically shaped body means and said first end of said cylindrically shaped body means;
  said first end of the second of said dual neck strap means being affixed to said cylindrically shaped body means at a point intermediate to said center portion of said cylindrically shaped body means and said second end of said cylindrically shaped body means;
  cooperating fastening means attached to said second end of said first and second neck strap means, respectively;
  said fastening means enabling the engagement of said second ends of said first and second neck strap means at selectable and adjustable positions, whereby the combined length of the combination of said first and second neck strap means and that portion of said cylindrically shaped body means intermediate to said points of affixation of said neck stap means may be selectively adjusted to be substantially equal to or greater than the diameter of said user's neck.

7. The invention according to claim 6 in which said fastening means attached to said second end of said first of said dual neck strap means comprising a multiplicity of loop means;
  said fastening means attached to said second end of said second of said dual neck strap means comprising a multiplicity of hook means;
  said multiplicity of hook means designed to cooperate with and removably engage said multiplicity of loop means, whereby said second ends of said first and second neck strap means may be selectively and repeatedly engaged and disengaged.

8. The invention according to claim 1 in which said attachment means comprises:
  dual head strap means for passing over the user's head, each of said head strap means having a respective first and second end;
  said first end of the first of said dual head strap means being affixed to said cylindrically shaped body means at a point intermediate to said center portion of said cylindrically shaped body means and said first end of said cylindrically shaped body means;
  said first end of the second of said dual head strap means being affixed to said cylindrically shaped body means at a point intermediate to said center portion of said cylindrically shaped body means and said second end of said cylindrically shaped body means;
  cooperating fastening means attached to said second end of said first and second head strap means, respectively;
  said fastening means enabling the engagement of said second ends of said first and second head strap means at selectable and adjustable positions, whereby the length of said head strap means may be adjusted to pass securely yet comfortably over said user's head.

9. The invention according to claim 8 in which said fastening means attached to said second end of said first of said dual head strap means comprising a multiplicity of loop means;
  said fastening means attached to said second end of said second of said dual head strap means comprising a multiplicity of hook means;
  said multiplicity of hook means designed to cooperate with and engage said multiplicity of loop means, whereby said second ends of said first and second head strap means may be selectively and repeatedly engaged and disengaged.

* * * * *